United States Patent
Jang et al.

(10) Patent No.: US 10,600,330 B2
(45) Date of Patent: Mar. 24, 2020

(54) METHOD AND APPARATUS FOR ASSESSING CARDIOPULMONARY FITNESS

(71) Applicant: Samsung Electronics Co., Ltd., Suwon-si (KR)

(72) Inventors: Dae-Geun Jang, Yongin-si (KR); Byunghoon Ko, Hwaseong-si (KR); SangKon Bae, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 151 days.

(21) Appl. No.: 15/243,547

(22) Filed: Aug. 22, 2016

(65) Prior Publication Data

US 2017/0282011 A1   Oct. 5, 2017

(30) Foreign Application Priority Data

Apr. 4, 2016 (KR) ........................ 10-2016-0040889

(51) Int. Cl.
| | |
|---|---|
| G09B 5/02 | (2006.01) |
| A61B 5/11 | (2006.01) |
| A61B 5/024 | (2006.01) |
| A61B 5/0205 | (2006.01) |
| A61B 5/00 | (2006.01) |
| G16H 50/30 | (2018.01) |
| G16H 20/30 | (2018.01) |

(52) U.S. Cl.
CPC .............. *G09B 5/02* (2013.01); *A61B 5/0205* (2013.01); *A61B 5/02438* (2013.01); *A61B 5/1118* (2013.01); *A61B 5/7271* (2013.01); *G16H 20/30* (2018.01); *G16H 50/30* (2018.01); *A61B 5/4866* (2013.01); *A61B 5/7275* (2013.01); *A61B 2560/029* (2013.01); *A61B 2560/0209* (2013.01)

(58) Field of Classification Search
None
See application file for complete search history.

(56) References Cited

U.S. PATENT DOCUMENTS

| | | | |
|---|---|---|---|
| 6,529,772 B2 | 3/2003 | Carlson et al. | |
| 9,049,999 B2 | 6/2015 | Kuroda et al. | |
| 2005/0209050 A1* | 9/2005 | Bartels | A63B 24/0084 482/8 |
| 2008/0161653 A1 | 7/2008 | Lin et al. | |
| 2008/0176719 A1* | 7/2008 | To | A63B 22/0235 482/54 |
| 2010/0197463 A1* | 8/2010 | Haughay, Jr. | A63B 24/0062 482/8 |

(Continued)

FOREIGN PATENT DOCUMENTS

| | | |
|---|---|---|
| JP | 3149050 B2 | 3/2001 |
| JP | 2002-253538 A | 9/2002 |

(Continued)

*Primary Examiner* — Jason T Yen
(74) *Attorney, Agent, or Firm* — NSIP Law

(57) ABSTRACT

A method and an apparatus for assessing cardiopulmonary fitness of a user are provided. A method of assessing cardiopulmonary fitness involves measuring a biosignal of a user performing an activity, measuring an exercise intensity of the activity, determining a parameter based on the biosignal and the exercise intensity, estimating a cardiopulmonary fitness index based on the parameter, and assessing the cardiopulmonary fitness of the user based on the cardiopulmonary fitness index.

23 Claims, 9 Drawing Sheets

(56) References Cited

U.S. PATENT DOCUMENTS

| | | | |
|---|---|---|---|
| 2011/0040193 A1 | 2/2011 | Seppanen et al. | |
| 2011/0190646 A1* | 8/2011 | Kato | A61B 5/02455 |
| | | | 600/500 |
| 2011/0288381 A1 | 11/2011 | Bartholomew et al. | |
| 2012/0010478 A1 | 1/2012 | Kinnunen et al. | |
| 2012/0029370 A1 | 2/2012 | Röcker et al. | |
| 2014/0052010 A1* | 2/2014 | Kasama | A61B 5/024 |
| | | | 600/508 |
| 2014/0087341 A1* | 3/2014 | Hall | G09B 5/065 |
| | | | 434/258 |
| 2014/0088444 A1 | 3/2014 | Saalasti et al. | |
| 2015/0209615 A1 | 7/2015 | Edwards | |
| 2015/0250417 A1 | 9/2015 | Cheng et al. | |
| 2015/0257656 A1 | 9/2015 | Konno et al. | |
| 2015/0297133 A1 | 10/2015 | Jouanique-Dubuis et al. | |
| 2015/0327804 A1* | 11/2015 | Lefever | A61B 5/0205 |
| | | | 600/483 |
| 2016/0227484 A1* | 8/2016 | Park | H04B 7/26 |
| 2016/0287177 A1* | 10/2016 | Huppert | A61B 5/6833 |
| 2017/0027801 A1* | 2/2017 | Choi | A61H 1/0244 |

FOREIGN PATENT DOCUMENTS

| | | |
|---|---|---|
| KR | 10-2009-0077419 A | 7/2009 |
| KR | 10-1030444 B1 | 4/2011 |
| KR | 10-2012-0067986 A | 6/2012 |
| KR | 10-1200061 B1 | 11/2012 |
| KR | 10-1301305 B1 | 9/2013 |
| KR | 10-1333511 B1 | 11/2013 |
| KR | 10-2014-0063330 A | 5/2014 |
| KR | 10-2014-0063374 A | 5/2014 |
| KR | 10-1398542 B1 | 5/2014 |
| KR | 10-1428780 B1 | 8/2014 |
| KR | 10-2015-0081171 A | 7/2015 |

\* cited by examiner

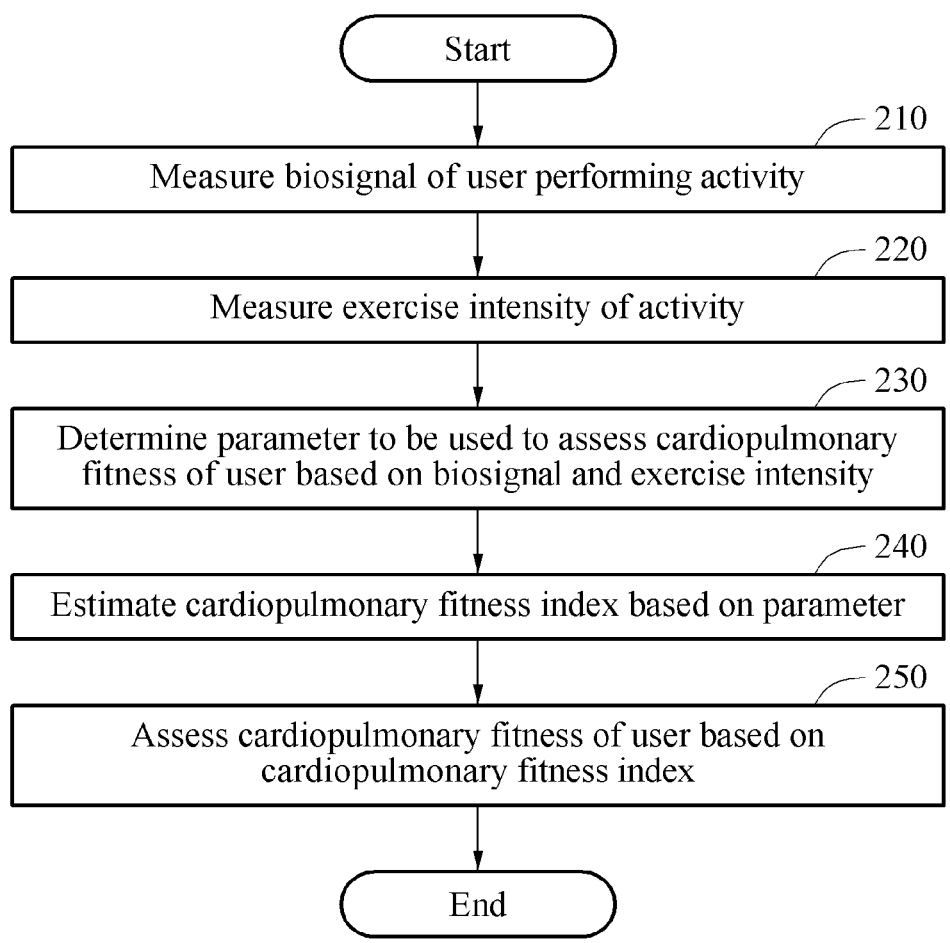

METHOD AND APPARATUS FOR ASSESSING CARDIOPULMONARY FITNESS

CROSS-REFERENCE TO RELATED APPLICATIONS

This application claims the benefit under 35 USC 119(a) of Korean Patent Application No. 10-2016-0040889 filed on Apr. 4, 2016, in the Korean Intellectual Property Office, the entire disclosure of which is incorporated herein by reference for all purposes.

BACKGROUND

1. Field

The following description relates to a method and an apparatus for assessing cardiopulmonary fitness.

2. Description of Related Art

There are numerous methods of measuring or assessing cardiopulmonary fitness of a person. For example, devices such as a blood glucose monitor or a gas measurement device may be used to assess the cardiopulmonary fitness of a person. However, in addition to the measurements taken by these devices, professional knowledge is required to analyze the measurement results to determine the cardiopulmonary fitness of a person. Thus, it is difficult for ordinary people to assess their cardiopulmonary fitness by using these devices.

The cardiopulmonary fitness of a person is accessed by determining a maximal exercise tolerance and/or submaximal exercise tolerance of the person based on the exercise capacity and fitness of the individual. An ordinary user who has difficulties in exercising at a submaximal exercise tolerance needs to use a designated exercise tolerance test protocol. In addition, such a user has a high risk of getting injured while exercising at a maximal exercise tolerance level. Thus, in practice, it is not easy for individuals to assess their own cardiopulmonary fitness and to implement an exercise regime.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of assessing cardiopulmonary fitness involves measuring a biosignal of a user performing an activity, measuring an exercise intensity of the activity, determining a parameter based on the biosignal and the exercise intensity, estimating a cardiopulmonary fitness index based on the parameter, and assessing the cardiopulmonary fitness of the user based on the cardiopulmonary fitness index.

The assessing of the cardiopulmonary fitness may be performed by a processor.

The measuring of the biosignal may involve measuring the biosignal in response to a determination that the biosignal reaches a preset threshold.

The measuring of the exercise intensity may involve measuring the exercise intensity in response to the determination that the biosignal reaches the preset threshold.

The general aspect of the method may further involve receiving an exercise perception level of the user, and the measuring of the biosignal may involve measuring the biosignal in response to a determination that the exercise perception level reaches a preset standard.

The measuring of the exercise intensity may involve measuring the exercise intensity in response to a determination that the exercise perception level reaches the preset standard.

The biosignal of the user may involve at least one of a heart rate, a respiration rate or both.

The exercise intensity may involve at least one of an exercise speed, an exercise distance, revolutions per minute (RPM) or a combination thereof.

The determining of the parameter may involve calculating the parameter based on a value obtained by dividing the biosignal by the exercise intensity.

The general aspect of the method may further involve receiving user information, and the estimating may involve estimating the cardiopulmonary fitness index based on at least one of the parameter, the user information or both.

The user information may include at least one of a gender, an age, a height, a weight, a waist measurement, a waist-hip ratio, a body mass index, or a physical activity level of the user.

The cardiopulmonary fitness index of the user may involve at least one of maximal oxygen consumption, a maximal heart rate, a ventilation threshold, a lactate threshold or a combination thereof.

The general aspect of the method may further involve comparing the assessed cardiopulmonary fitness to a preset cardiopulmonary fitness reference value, and providing the user with a result of the comparing.

The general aspect of the method may further involve estimating a metabolic disease risk index of the user based on the assessed cardiopulmonary fitness of the user, and providing the user with a health care prescription based on the metabolic disease risk index of the user.

The general aspect of the method may further involve generating a personalized exercise program for the user based on the assessed cardiopulmonary fitness of the user, and providing the user with the personalized exercise program.

The general aspect of the method may further involve receiving preference information of the user, and the generating of the personal exercise program may involve selecting a template from preset exercise program templates based on the preference information, adjusting an exercise intensity and an exercise duration of the selected template based on the assessed cardiopulmonary fitness of the user, and generating the personalized exercise program based on the adjusted exercise intensity and the adjusted exercise duration of the selected template.

In another general aspect, a non-transitory computer-readable medium may store instructions that, when executed by a processor, cause the processor to perform a method described above.

In another general aspect, an apparatus for assessing cardiopulmonary fitness includes a measurer configured to measure a biosignal of a user performing an activity and measure an exercise intensity of the activity, and a processor configured to determine a parameter based on the biosignal and the exercise intensity and assess the cardiopulmonary fitness of the user based on a cardiopulmonary fitness index estimated based on the parameter.

The processor may be configured to determine whether the biosignal reaches a preset threshold, and the measurer may be configured to measure the biosignal and the exercise intensity of the activity in response to a determination that the biosignal reaches the preset threshold.

The general aspect of the apparatus may further include an input device configured to receive an exercise perception level of the user, and the processor may be configured to determine whether the exercise perception level reaches a preset standard, and the measurer may be configured to measure the biosignal and the exercise intensity of the activity in response to a determination that the exercise perception level reaches the preset standard.

The general aspect of the apparatus may further include a communication interface configured to receive user information, wherein the processor may be configured to determine the parameter based on a value obtained by dividing the biosignal by the exercise intensity and estimate the cardiopulmonary fitness index of the user based on at least one of the parameter, the user information or both.

In yet another general aspect, a method of assessing cardiopulmonary fitness involves: receiving a biosignal measured by a sensor while a user performing an activity; determining an exercise intensity of the activity; and assessing, by a processor, the cardiopulmonary fitness of the user based on the biosignal and the exercise intensity.

The assessing of the cardiopulmonary fitness may involve obtaining a value corresponding to the biosignal divided by the exercise intensity.

The assessing of the cardiopulmonary fitness may involve calculating a relative heart rate of the user based on the biosignal and the exercise intensity, and estimating a cardiopulmonary fitness index of the user based on user information.

The determining of the exercise intensity may involve receiving information from one or more sensors of a wearable device during the activity, and calculating the exercise intensity from the received information.

Other features and aspects will be apparent from the following detailed description, the drawings, and the claims.

BRIEF DESCRIPTION OF THE DRAWINGS

FIG. 2 is a flowchart illustrating an example of a method of assessing cardiopulmonary fitness.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1A:
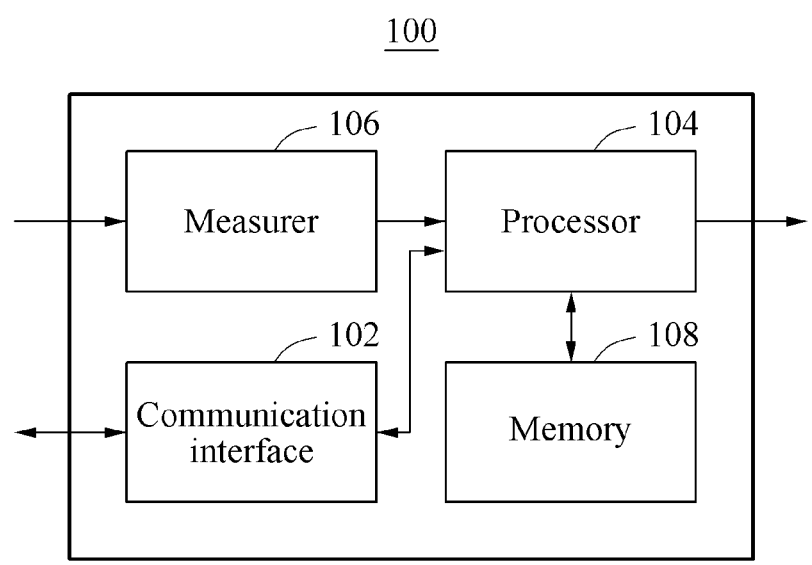
FIG. 1A is a block diagram illustrating an example of an apparatus for assessing cardiopulmonary fitness.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of this disclosure. For example, the sequences of operations described herein are merely examples, and are not limited to those set forth herein, but may be changed as will be apparent after an understanding of this disclosure, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of this disclosure.

Terms such as "first," "second," "A," "B," "(a)," "(b)," and the like may be used herein to describe components. Each of these terminologies is used merely to distinguish a component from another corresponding component, and not to define an essence or to order or sequence of the components. For example, a first component may be referred to a second component, and similarly the second component may also be referred to as the first component.

It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Set forth hereinafter are examples of apparatuses and methods that may be used to assess cardiopulmonary fitness of a user or to generate and provide a personalized exercise program based on a result of the assessment. The examples of apparatuses and methods may be implemented in various types of products. For example, the apparatuses and methods may be implemented in personal computers, laptop computers, tablet computers, smart phones, smart home appliances, and wearable devices. Alternately, the apparatuses and methods may be applied to a smart phone, a mobile device, a smart home system, and a wearable device to assess cardiopulmonary fitness of a user performing a self-regulated activity and provide a result of assessing the cardiopulmonary fitness. Further, the examples of apparatuses and methods may be provided in an exercise coaching program to generate a personalized exercise prescription based on cardiopulmonary fitness and an exercise capacity of an individual, or to conveniently measure cardiopulmonary fitness and an exercise capacity of an individual in a home health care system. Hereinafter, the examples will now be described with reference to the accompanying drawings, wherein like reference numerals refer to like elements throughout the description.

Figure 1B:
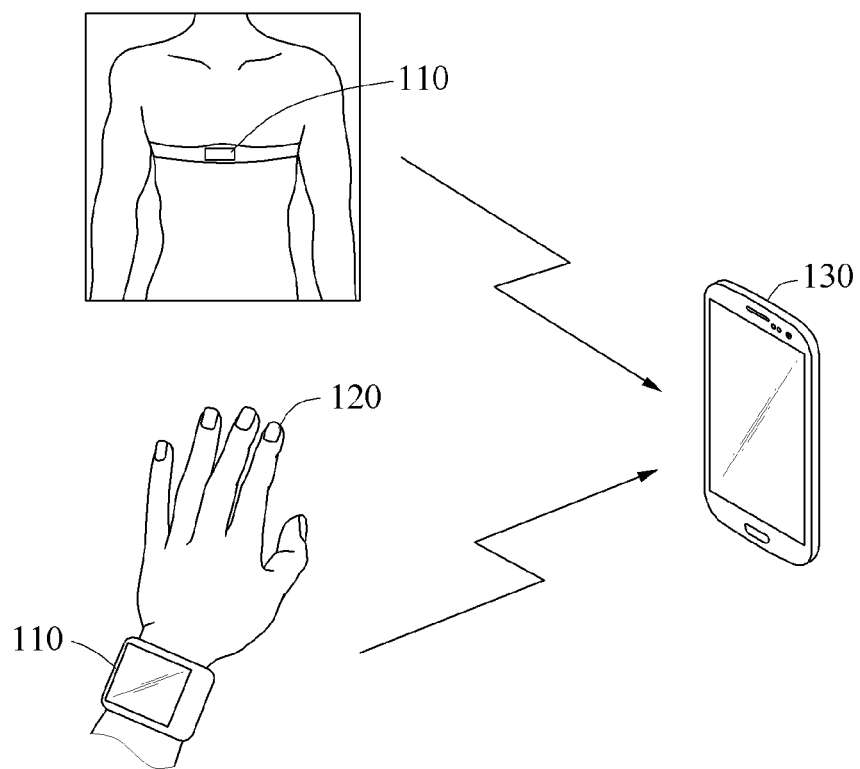
FIG. 1B illustrates an operation of an example of an apparatus for assessing cardiopulmonary fitness.

FIG. 1A illustrates an example of an apparatus for assessing cardiopulmonary fitness, and FIG. 1B illustrates an example of an operation of an apparatus for assessing cardiopulmonary fitness. The example of an apparatus 100 for assessing cardiopulmonary fitness illustrated in FIG. 1A is hereinafter referred to as the "assessing apparatus" 100. FIG. 1B illustrates two different types of devices that include an example of an assessing apparatus 100.

Referring to FIG. 1A, the assessing apparatus 100 includes a communication interface 102, a processor 104, a measurer 106, and a memory 108. In this example, the communication interface 102, the processor 104, the measurer 106, and the memory 108 are implemented with hardware components. The communication interface 102, the processor 104, the measurer 106, and the memory 108 communicate with one another through a bus (not shown).

The communication interface 102 receives user information. The user information includes, for example, a gender, an age, a height, a weight, a waist measurement, a waist-hip ratio (WHR), a body mass index (BMI), a physical activity level, or a condition of a user.

The communication interface 102 receives information from an external device, or provides information related to cardiopulmonary fitness of a user, which is assessed by the processor 104, to an external device. Further, the communication interface 102 receives preference information of the user. The preference information of the user includes information related to an exercise intensity, an exercise duration, and an exercise type such as an exercise program which are preferred by the user. The preference information may be manually input by the user via a touchscreen or keypad or input by the user via a microphone and voice recognition, for example.

In an example, the assessing apparatus 100 may further include an input device (not shown) to receive a variety of information directly from the user. The assessing apparatus 100 receives from the user, through the input device, an exercise perception level of the user, the preference information of the user, exercise information of the user, and the user information. The input device includes a graphical user interface (GUI), a touchscreen, a key pad, a microphone or the like$_{[LC1]}$.

The processor 104 determines or calculates a parameter to be used to assess the cardiopulmonary fitness of the user based on a result of measurement performed by the measurer 106. The processor 104 estimates a cardiopulmonary fitness index based on at least one of the parameter or the user information. The processor 104 assesses the cardiopulmonary fitness of the user based on the cardiopulmonary fitness index.

The measurer 106 measures a biosignal of the user while the user is performing a self-regulated activity. Here, the term "self-regulated activity" includes all self-regulated motions and activities performed by a user during daily life. The self-regulated activity includes, for example, daily activities which are not subject to a cardiopulmonary fitness test. Examples of these daily activities include going to work, working, eating, coming home, shopping, taking a walk, and taking care of children. In addition, a self-regulated activity also includes exercises which are subject to a cardiopulmonary fitness test. Examples of the exercises include a graded tolerance exercise, a low-intensity exercise, a mid-intensity exercise, and a high-intensity exercise that are performed during a cardiopulmonary fitness test. The measurer 106 measures an exercise intensity of the self-regulated activity.

The measurer 106 may include a single sensor or a plurality of sensors. The sensor(s) are used to measure the biosignal of the user performing the self-regulated activity and the exercise intensity of the self-regulated activity.

The measurer 106 measures a biosignal of the user by using, for example, an electromyography (EMG) sensor, an electrocardiography (ECG) sensor, a photoplethysmography (PPG) sensor, a heart rate sensor, a sensor that measures a change in blood flow rate using an ultrasonic Doppler scheme or laser Doppler scheme, or a temperature measuring sensor. Examples of biosignals that may be measured by the measurer 106 include heart rate signals, EMG signals, respiration signals measured in succession and the like.

Further, the measurer 106 measures a motion of the user and the exercise intensity of the self-regulated activity using a global positioning system (GPS) sensor, and an inertial sensor such as an acceleration sensor, a gyro sensor, a strain sensor, a shock sensor, or a tilt sensor, for example. However, examples of sensors suitable for use in a measurer 106 are not limited thereto. The measurer 106 may include various other sensors.

The processor 104 determines whether a biosignal reaches a preset threshold. In response to a determination that a biosignal reaches the preset threshold, the processor 104 controls the measurer 106 to measure the biosignal and determine the exercise intensity of the self-regulated activity.

The processor 104 may also determine whether the exercise perception level input through an input device reaches a preset standard. In response to a determination that the exercise perception level reaches a preset standard, such as a mid-level intensity or a scale of "5" according to revised Borg's rating of perceived exertion (RPE) scale, for example, the processor 104 controls the measurer 106 to measure the biosignal and determine the exercise intensity of the self-regulated activity being monitored.

According to an example, the processor 104 calculates a parameter to be used to assess the cardiopulmonary fitness of the user based on a value obtained by dividing a magnitude of a biosignal by a value representing an exercise intensity. The parameter may be, for example, a relative physiological parameter such as a relative heart rate. The processor 104 estimates a cardiopulmonary fitness index of a user by substituting at least one of the parameter or the user information into a regression equation.

The memory 108 stores the estimated cardiopulmonary fitness index of the user and a result of assessing the cardiopulmonary fitness. Further, the memory 108 stores the user information, the preference information of the user, and the exercise information of the user. The memory 108 may be a non-transitory memory, a non-volatile memory, or a volatile memory.

In addition, according to this example, the processor 104 performs at least one of the methods to be described below with reference to FIGS. 2 through 8. The processor 104 executes a program, and controls the assessing apparatus 100. A program code to be executed by the processor 104 is stored in the memory 108. The assessing apparatus 100 is connected to an external device such as, for example, a personal computer or a network, through an input/output device (not shown), and exchanges data with the external device.

The examples of methods described with reference to FIG. 1A through FIG. 8 may be implemented in a form of an application to be executed by a processor in a tablet computer, a smart phone, or a wearable device, or may be implemented in a form of a chip and embedded in a smart phone or a wearable device.

Referring to FIG. 1B, a wearable device 110 may include an assessing apparatus 100, and the wearable device 110 communicates with a mobile device 130.

An operation of an example of an assessing apparatus 100 included in the wearable device 110 will be described. For example, the wearable device 110 may include a wrist-worn device provided in a shape of a watch or a bracelet, a necklace-shaped device, a chest-worn device, and other devices provided in various shapes that may be worn by a user during daily life.

When a user 120 performs an activity while wearing the wearable device 110, the assessing apparatus 100 may receive user information directly through the wearable device 110 or receive the user information from an external device.

In this example, the assessing apparatus 100 measures a biosignal generated when the user 120 performs a self-regulated activity and determines an exercise intensity of the self-regulated activity using sensor(s) included in the wearable device 110.

The assessing apparatus 100 determines a parameter to be used to assess cardiopulmonary fitness of the user 120 based on the measured biosignal and the measured exercise intensity. The assessing apparatus 100 estimates a cardiopulmonary fitness index based on the parameter and the user information, and assesses the cardiopulmonary fitness of the user 120 based on the cardiopulmonary fitness index.

The assessing apparatus 100 estimates a metabolic disease risk index of the user 120 based on a result of assessing the cardiopulmonary fitness of the user 120, and provides the user 120 with a health care prescription. Further, the assessing apparatus 100 generates a personalized exercise program for the user 120 based on a result of assessing the cardiopulmonary fitness of the user 120, and provides the user 120 with the personalized exercise program. The assessing apparatus 100 may provide the user 120 with the personalized exercise program through the wearable device 110.

The assessing apparatus 100 of the wearable device 110 interoperates with the mobile device 130, and shares data with the mobile device 130. For example, a signal measured from the user 120 through the wearable device 110 is transmitted to the mobile device 130.

In another example, the processor 104 of the assessing apparatus 100 is embedded in the mobile device 130, and the measurer 106 of the assessing apparatus 100 is embedded in the wearable device 110. The wearable device 110 is worn on a body part, for example, a wrist or a chest, of the user 120 to measure a biosignal of the user that is generated when the user 120 performs a self-regulated activity and an exercise intensity of the self-regulated activity. The wearable device 110 amplifies and filters the measured biosignal. The wearable device 110 transmits the measured biosignal to the mobile device 130.

In this example, the mobile device 130 determines a parameter to be used to assess cardiopulmonary fitness of the user 120 based on the biosignal and the exercise intensity measured by the wearable device 110. The mobile device 130 estimates a cardiopulmonary fitness index based on the parameter and user information input through the wearable device 110 or the mobile device 130, and assesses the cardiopulmonary fitness of the user 120 based on the cardiopulmonary fitness index. The mobile device 130 provides the user 120 with a result of assessing the cardiopulmonary fitness through a display or audio device of the mobile device 130 or the wearable device 110.

The wearable device 110 and the mobile device 130 may be connected to each other through a wireless link. The wearable device 110 and the mobile device 130 may each include wireless Internet interfaces such as a wireless local area network (WLAN), a wireless fidelity (Wi-Fi) direct, a digital living network alliance (DLNA), a wireless broadband (WiBro), a world interoperability for microwave access (WiMAX), and a high speed downlink packet access (HSDPA), for example, and short-range communication interfaces such as Bluetooth, a radio frequency identification (RFID), an infrared data association (IrDA), a ultra wideband (UWB), ZigBee, and a near field communication (NFC).

The mobile device 130 may be implemented as a tablet computer, a smart phone, a personal digital assistant (PDA), or the like. The mobile device 130 may be network equipment such as a server. The mobile device 130 may be a single server computer or a system similar thereto, or at least one server bank or server cloud distributed at different geographical locations.

The mobile device 130 may receive various biosignals from the wearable device 110 or other measuring devices.

FIG. 2 is a flowchart illustrating an example of a method of assessing cardiopulmonary fitness.

Referring to FIG. 2, in operation 210, an assessing apparatus measures a biosignal of a user performing a self-regulated activity. As described above, a self-regulated activity includes all motions and activities that may be performed during daily life. Examples of self-regulated activities include daily activities, such as going to work, working, eating, coming home, shopping, taking a walk, taking care of children and the like. Examples of graded tolerance exercises include a treadmill, a bicycle ergometer, and a bench step, and graded tolerance daily exercises such as running, jogging, walking, step climbing, and swimming.

The assessing apparatus measures a biosignal of a user using, for example, an EMG sensor, an ECG sensor, a PPG sensor, a heart rate sensor, or a sensor that measures a change in a blood flow rate using an ultrasonic Doppler scheme or laser Doppler scheme. The biosignal of the user includes a heart rate or a respiration rate of the user.

In operation 220, the assessing apparatus measures an exercise intensity of a self-regulated activity. The assessing apparatus measures the exercise intensity of the self-regulated activity being performed by the user by using an inertial sensor such as an acceleration sensor, a gyro sensor, a strain sensor, a shock sensor, or a tilt sensor, for example. The exercise intensity of the self-regulated activity includes, for example, an exercise speed, an exercise distance, and revolutions per minute (RPM) of the self-regulated activity. The assessing apparatus measures the biosignal and the exercise intensity simultaneously or at different points in time.

In operation 230, the assessing apparatus determines a parameter to be used to assess cardiopulmonary fitness of the user based on the biosignal and the exercise intensity. For example, the assessing apparatus determines the parameter based on a value obtained by dividing the biosignal, for example, a heart rate, by the exercise intensity. According to one example, the value of the parameter is calculated based on the equation "parameter=heart rate/exercise intensity," which may be called a relative heart rate. However, depending on the biosignals that are measured, a different equation may be used to calculate the parameter.

In operation 240, the assessing apparatus estimates a cardiopulmonary fitness index based on the parameter. The assessing apparatus estimates the cardiopulmonary fitness index of the user by substituting the parameter into a regression equation. Examples of cardiopulmonary fitness indices that may be used include maximal oxygen consumption $VO_2max$, a maximal heart rate HRmax, a ventilation threshold, a lactate threshold and the like. The maximal oxygen consumption refers to oxygen consumption that is reached when oxygen consumption remains at a steady state despite an increase in exercise intensity. The ventilation threshold refers to an exercise intensity at which $VE/VO_2$ starts to increase at a faster rate than $VE/VCO_2$ as an exercise tolerance increases. The lactate threshold refers to a point at which a concentration of lactic acid begins to exponentially increase in response to an increase in exercise intensity in a relationship between the exercise intensity and the concentration of lactic acid.

In operation 250, the assessing apparatus assesses the cardiopulmonary fitness of the user based on the cardiopulmonary fitness index.

Figure 3:
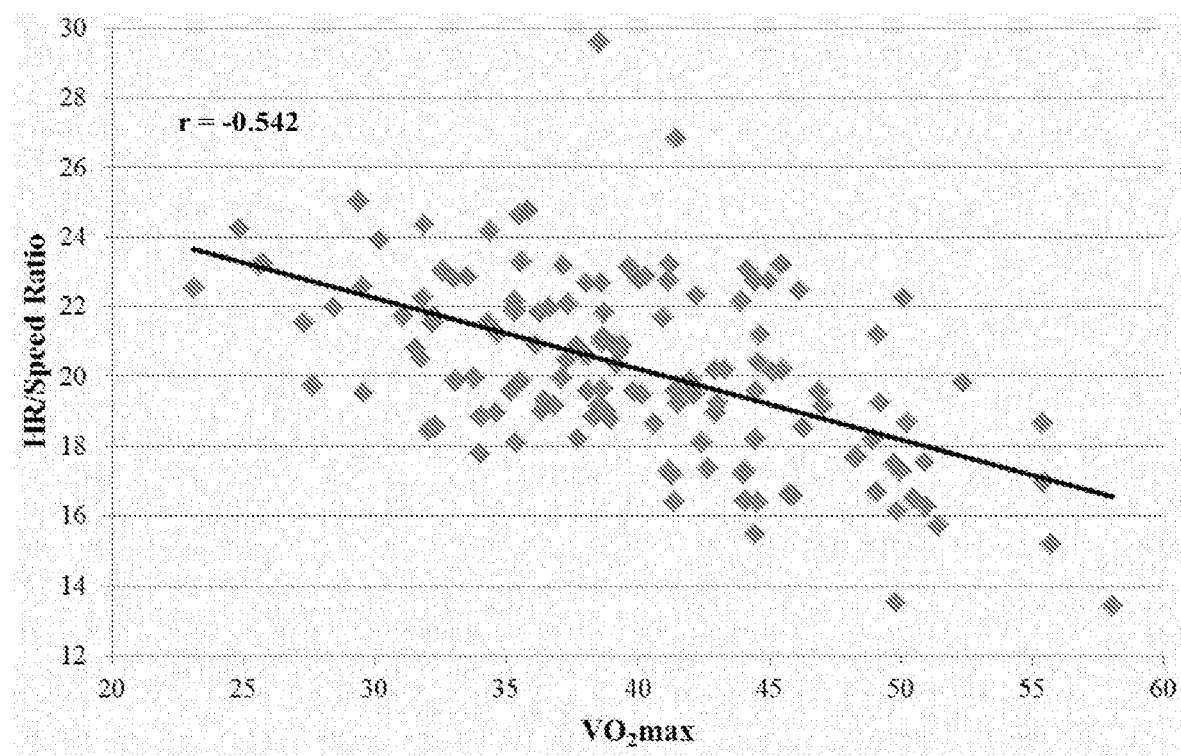
FIG. 3 is a graph illustrating a relationship between a parameter and a cardiopulmonary fitness index according to an example of a method of assessing cardiopulmonary fitness.

FIG. 3 illustrates an example of a relationship between a parameter and a cardiopulmonary fitness index according to an example of the apparatus for assessing cardiopulmonary fitness. Referring to FIG. 3, a relationship between a parameter and maximal oxygen consumption $VO_2max$ is illustrated as one of cardiopulmonary fitness indices measured while a user is performing a low-intensity exercise. Here, the parameter is a relative heart rate that is calculated based on the equation "relative heart rate=heart rate/exercise intensity."

In the graph of FIG. 3, an X-axis corresponds to the maximal oxygen consumption. A Y-axis corresponds to the relative heart rate obtained by dividing the heart rate HR by the exercise intensity. The exercise intensity is a running speed.

According to the graph illustrated in FIG. 3, the relative heart rate and the maximal oxygen consumption have an inverse proportional relationship. In this example, the slope of the graph corresponds to a correlation r of −0.542. Thus, the relationship between the relative heart rate and the maximal oxygen consumption may be used to estimate the cardiopulmonary fitness or exercise capacity of the user.

Figure 4:
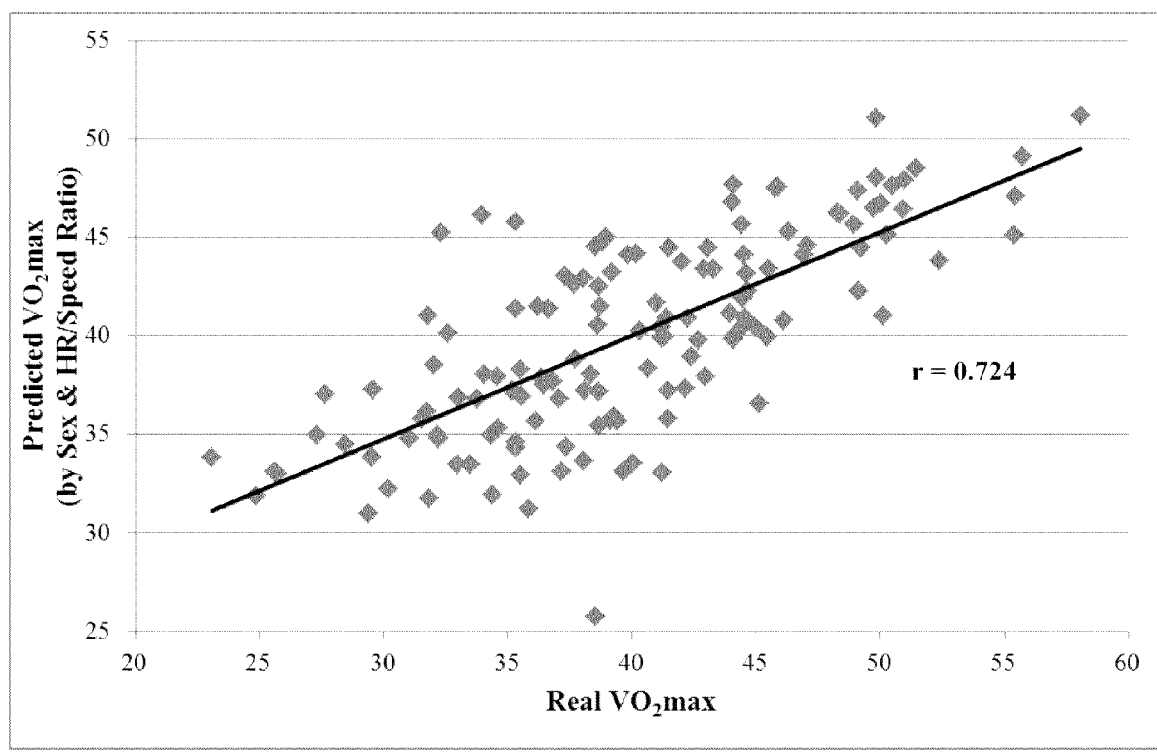
FIG. 4 is a graph illustrating a relationship between a cardiopulmonary fitness index with user information and a parameter according to an example of a method of assessing cardiopulmonary fitness.

FIG. 4 illustrates a graph demonstrating a relationship between a parameter and a cardiopulmonary fitness index with respect to a user having certain user information. Referring to FIG. 4, a cardiopulmonary fitness index, for example, $VO_2max$, estimated based on the relative heart rate and the gender of a user, and a real cardiopulmonary fitness index, for example, $VO_2max$, are measured. The predicted cardiopulmonary fitness index and the real cardiopulmonary fitness index measured from a plurality of users have a mathematical relationship corresponding to a correlation r of 0.724. In the graph of FIG. 4, the X-axis denotes the real cardiopulmonary fitness index, and the Y-axis denotes the cardiopulmonary fitness index estimated based on the relative heart rate and the gender of the user.

Cardiopulmonary fitness level shows a significant difference based on the gender of the user. For example, in general, a male user has a higher maximal oxygen consumption than a female user.

In an example, user information having a significant correlation of a cardiopulmonary fitness index of a user, such as a gender, and a relative heart rate, may be used to assess cardiopulmonary fitness of a user. For example, when the user is a male and has a low relative heart rate in comparison to a predetermined heart rate value, the user may have a cardiopulmonary fitness level higher than a predetermined standard. When the user is a female and has a high relative heart rate in comparison to a predetermined heart rate value, the user may have a cardiopulmonary fitness level lower than the predetermined standard.

An assessing apparatus estimates a cardiopulmonary fitness index of a user by using a cardiopulmonary fitness estimating equation represented as, for example, "cardiopulmonary fitness index ($VO_2max$)=a+b× user information (male: 1, female: 0)−c× relative heart rate."

In an example, the cardiopulmonary fitness of a user is assessed based on a correlation between a relative heart rate and a cardiopulmonary fitness index or between a relatively high correlation of a cardiopulmonary fitness index with user information and a relative heart rate.

Figure 5:
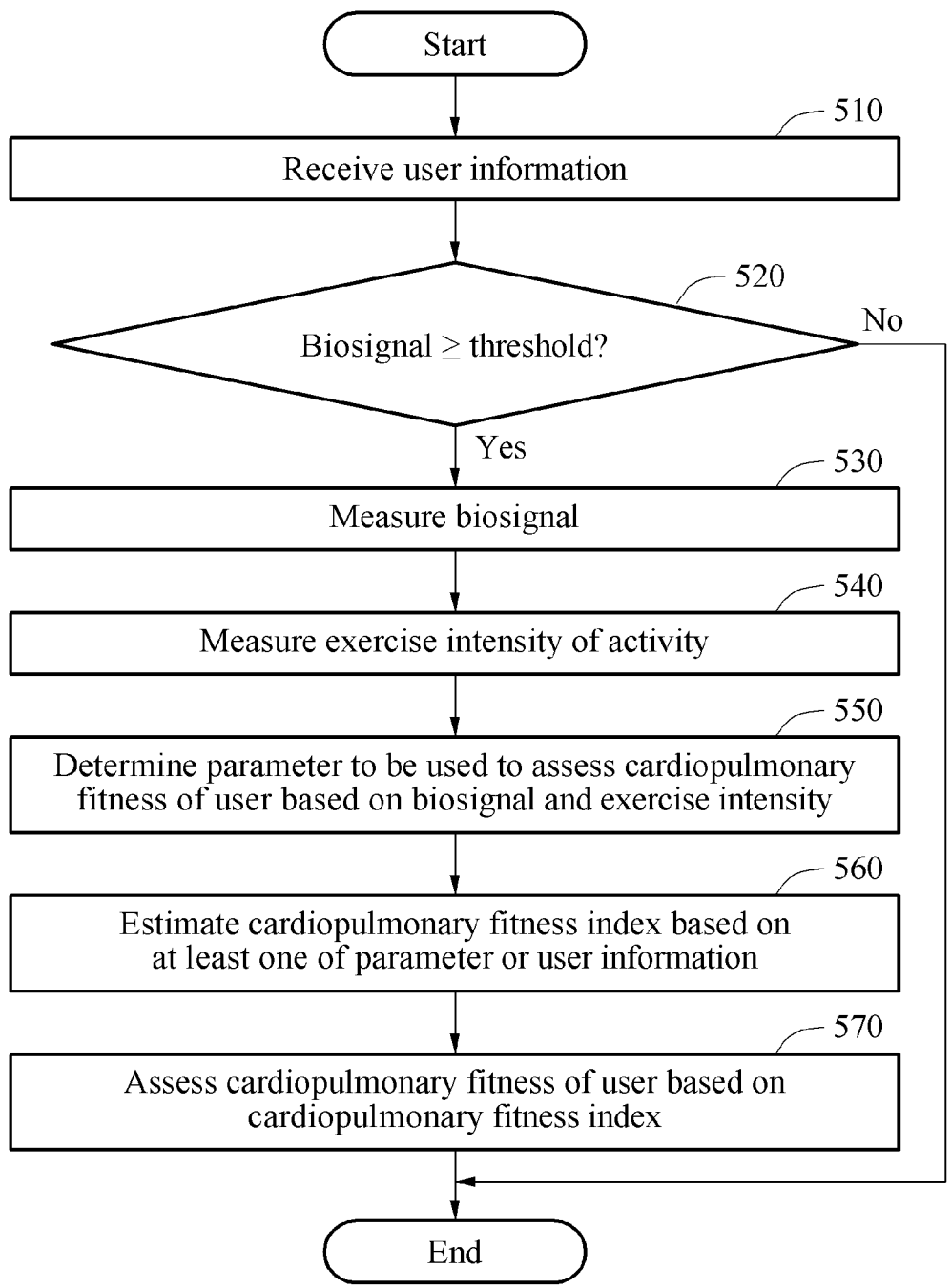
FIGS. 5 through 8 are flowcharts illustrating examples of methods of assessing cardiopulmonary fitness.

FIG. 5 is a flowchart illustrating an example of a method of assessing cardiopulmonary fitness. Referring to FIG. 5, an example of a method of automatically performing a cardiopulmonary fitness assessment while a user is performing daily routine without being aware of the assessment of cardiopulmonary fitness or while the user does not have an intent to assess cardiopulmonary fitness.

In operation 510, an assessing apparatus receives user information.

In operation 520, the assessing apparatus determines whether a biosignal of a user who is performing a self-regulated activity reaches a preset threshold value. In response to a determination that the biosignal does not reach the threshold value, the assessing apparatus is maintained in a power saving mode. According to an example, the assessing apparatus is maintained in the power saving mode until the biosignal reaches the preset threshold or terminates an operation. In an example, the biosignal is determined to have reached the preset threshold value when a magnitude of the biosignal is equal to or greater than the preset threshold $value_{[LC2]}$.

In response to a determination that the biosignal reaches the threshold, the assessing apparatus measures the biosignal in operation 530, and measures an exercise intensity of the self-regulated activity in operation 540.

In operation 550, the assessing apparatus determine a parameter such as, for example, a relative heart rate, to be used to assess cardiopulmonary fitness of the user based on the biosignal and the exercise intensity.

In operation 560, the assessing apparatus estimates a cardiopulmonary fitness index based on at least one of the parameter or the user information.

In operation 570, the assessing apparatus assesses the cardiopulmonary fitness of the user based on the estimated cardiopulmonary fitness index.

For example, a user wearing an assessing apparatus may starting running in order to catch a subway or a bus during the morning rush hour. When a heart rate of the user reaches a preset threshold, for example, 110 beats per minute (bpm) due to the running, the assessing apparatus may automatically measure a heart rate and an exercise intensity, for example, a running speed, from the corresponding point in time the preset threshold is reached. The assessing apparatus may estimate a cardiopulmonary fitness index of the user by applying user information and a relative heart rate obtained based on the heart rate of the user and the exercise intensity to a cardiopulmonary fitness estimating equation. In this example, the user information is received or input beforehand through the assessing apparatus. The assessing apparatus assesses the cardiopulmonary fitness of the user by comparing the estimated cardiopulmonary fitness index to cardiopulmonary fitness standards preset by gender or age.

In an example, cardiopulmonary fitness of a user may be assessed based on a normal activity of the user during daily life without monitoring the cardiopulmonary fitness by setting aside a separate exercise session, using a specialized device, or setting aside a designated time period to assess the cardiopulmonary fitness.

Figure 6:
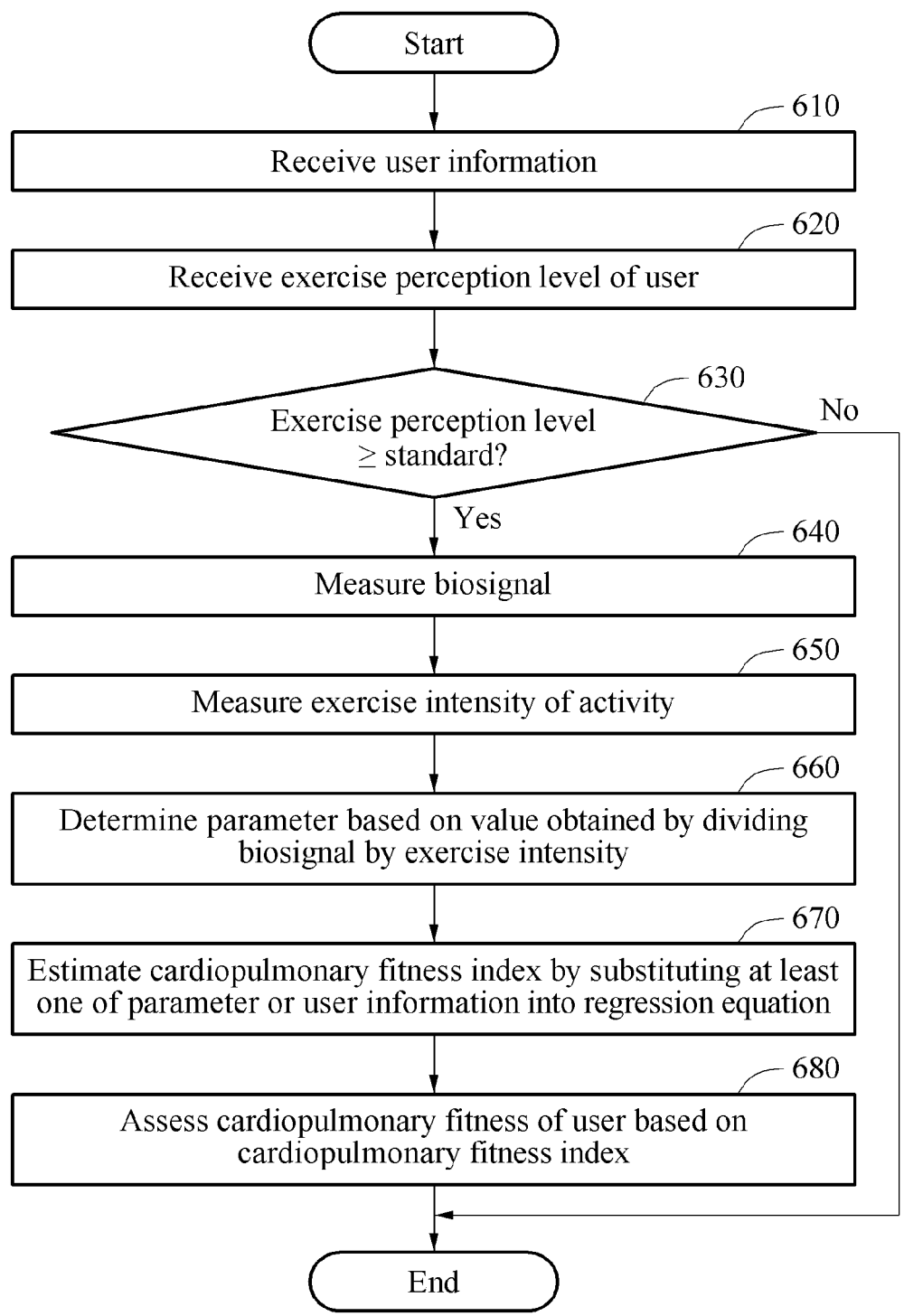

FIG. 6 is a flowchart illustrating an example of a method of assessing cardiopulmonary fitness. Referring to FIG. 6, an example of a method of performing a cardiopulmonary fitness assessment by setting an exercise perception level while a user has an intent to assess his or her cardiopulmonary fitness is illustrated.

In operation 610, an assessing apparatus receives user information. In this example, the user information is received before a user performs an exercise.

In operation 620, the assessing apparatus receives an exercise perception level of the user. The assessing apparatus receives the exercise perception level from the user performing an activity with an intent to assess cardiopulmonary fitness.

The exercise perception level refers to a level of physical effort as perceived or subjectively experienced by a user who is performing an exercise. The exercise perception level is affected by, for example, a fitness level of the user, an environment level, or a general fatigue level.

The exercise perception level may be represented by, for example, Borg's scale, OMNI scale, Likert scale, and/or visual analogue scale. Table 1 shows Borg's scale, and Table 2 shows OMNI scale.

TABLE 1

| Borg's Category Scale (Original) | | Borg's Category-Ratio Scale (Revised) | |
|---|---|---|---|
| Scale | Description | Scale | Description |
| 6 | | 0 | Nothing at all |
| 7 | Very, very light | 0.3 | |
| 8 | | 0.5 | Extremely weak    Just noticeable |
| 9 | Very light | 0.7 | |
| 10 | | 1 | Very weak |
| 11 | Fairly light | 1.5 | |
| 12 | | 2 | Weak    Light |
| 13 | Somewhat hard | 2.5 | |
| 14 | | 3 | Moderate |
| 15 | Hard | 4 | |
| 16 | | 5 | Strong    Heavy |
| 17 | Very hard | 6 | |
| 18 | | 7 | Very strong |
| 19 | Very, very hard | 8 | |
| 20 | | 9 | |
| | | 10 | Extremely strong    Maximal |
| | | 11 | |

TABLE 2

| for Adults | | for Children | |
|---|---|---|---|
| 0 | Extremely easy | 0 | Not tired at all |
| 1 | | 1 | |
| 2 | Easy | 2 | Little tired |
| 3 | | 3 | |
| 4 | Somewhat easy | 4 | Getting more tired |
| 5 | | 5 | |
| 6 | Somewhat hard | 6 | Tired |
| 7 | | 7 | |
| 8 | Hard | 8 | Really tired |
| 9 | | 9 | |
| 10 | Extremely hard | 10 | Very, very tired |

In the original Borg's scale, an exercise perception level corresponding to a maximal exercise intensity is expressed by a scale of "19" or "20". In the revised Borg's scale and OMNI scale, the exercise perception level corresponding to the maximal exercise intensity is expressed by a scale of "10".

According to an example, an assessing apparatus uses OMNI scale as shown in Table 2. The assessing apparatus inquires about an exercise perception level with respect to an exercise or a self-regulated activity currently being performed by a user through a screen of a display or a speaker. For example, the screen may display the statement: "How is the exercise intensity?" Likewise, a speaker may produce an audio sound corresponding to "How is the exercise intensity?" The assessing apparatus guides the user to select one from "extremely hard, hard, somewhat hard, somewhat easy, easy, and extremely easy" or "levels 0 to 10". The assessing apparatus receives an exercise perception level selected by the user as guided.

In operation 630, the assessing apparatus determines whether the exercise perception level reaches a preset standard. In response to a determination that the exercise perception level does not reach the preset standard, the assessing apparatus remains in a power saving mode until the exercise perception level reaches the preset standard, or terminates an operation. In an example, the exercise perception level is determined to have reached the preset standard when the exercise perception level is equal to or greater than the preset standard$_{[LC3]}$.

In response to a determination that the exercise perception level reaches the preset standard, the assessing apparatus measures a biosignal in operation 640, and measures an exercise intensity of a self-regulated activity in operation 650.

In operation 660, the assessing apparatus determines a parameter, for example, a relative heart rate, based on a value obtained by dividing the biosignal by the exercise intensity.

In operation 670, the assessing apparatus estimates a cardiopulmonary fitness index by substituting at least one of the parameter or the user information into a regression equation, for example, a cardiopulmonary fitness estimating equation. The regression equation may be expressed as, for example, Y (cardiopulmonary fitness index)=$\alpha \times X$ (parameter)+$\beta$, Y=$\alpha 1 \times X1$ (parameter)+$\alpha 2 \times X2$ (user information: gender)+$\beta$, or Y=$\alpha 1 \times X1$ (parameter)+$\alpha 2 \times X2$ (user information: gender)+$\alpha 3 \times X3$ (user information: BMI)+$\beta$. In this example, the coefficients $\alpha$, $\alpha 1$, $\alpha 2$, $\alpha 3$, and $\beta$ are determined differently based on a cardiopulmonary fitness index Y to be estimated by the assessing apparatus, a parameter to be used, and user information to be used.

In operation 680, the assessing apparatus assesses the cardiopulmonary fitness of the user based on the cardiopulmonary fitness index.

Figure 7:
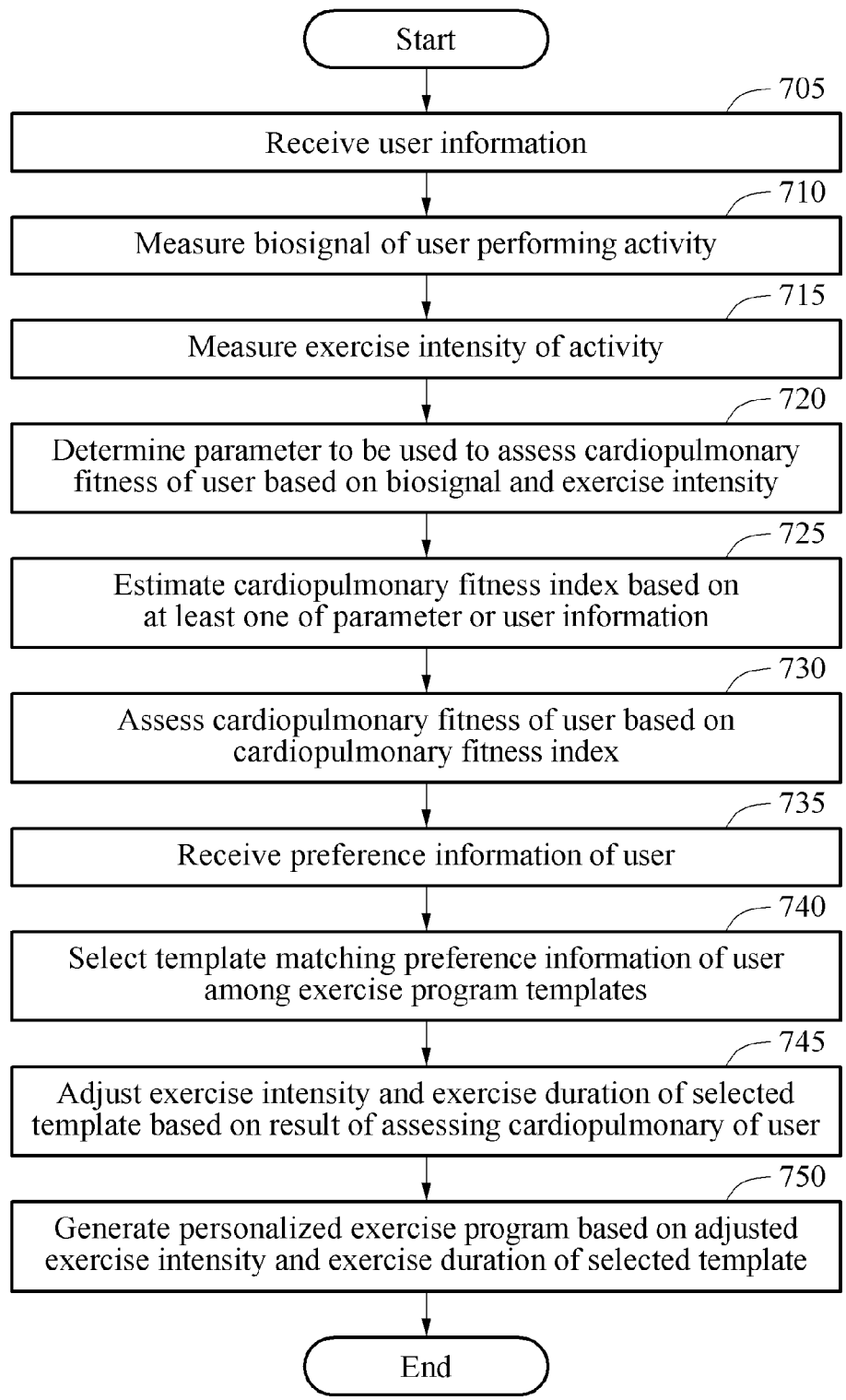

FIG. 7 is a flowchart illustrating an example of a method of assessing cardiopulmonary fitness.

Referring to FIG. 7, in operation 705, an assessing apparatus receives user information.

In operation 710, the assessing apparatus measures a biosignal of a user performing a self-regulated activity.

In operation 715, the assessing apparatus measures an exercise intensity of the self-regulated activity.

In operation 720, the assessing apparatus determines a parameter, for example, a relative heart rate, to be used to assess cardiopulmonary fitness of the user based on the biosignal and the exercise intensity.

In operation 725, the assessing apparatus estimates a cardiopulmonary fitness index based on at least one of the parameter or the user information.

In operation 730, the assessing apparatus assesses the cardiopulmonary fitness of the user based on the estimated cardiopulmonary fitness index. The assessing apparatus generates a personalized exercise program for the user based on a result of assessing the cardiopulmonary fitness of the user, and provides the user with the personalized exercise program. For example, when the cardiopulmonary fitness of the user is assessed at about 60% of that of an ordinary person, the assessing apparatus generates an exercise program corresponding to an exercise intensity of about 60% of that of an ordinary person, and provides the user with the exercise program.

Further, the assessing apparatus generates the personalized exercise program based on preference information of the user. In operation 735, the assessing apparatus receives the preference information of the user. The preference information of the user includes an exercise type, an exercise duration, and an exercise intensity preferred by the user.

In operation 740, the assessing apparatus selects a template matching the preference information of the user from preset exercise program templates. The exercise program templates are pre-stored in a template database (DB). The template DB is stored in a memory of the assessing apparatus or an external storage device.

In operation 745, the assessing apparatus adjusts an exercise intensity and an exercise duration of the selected template based on a result of assessing the cardiopulmonary fitness of the user. In response to a determination that the cardiopulmonary fitness of the user is higher or lower than that of an ordinary person as a result of assessing the cardiopulmonary fitness of the user, the assessing apparatus increases or decreases the exercise intensity and the exercise duration of the selected template.

In operation 750, the assessing apparatus generates the personalized exercise program based on the adjusted exercise intensity and the adjusted exercise duration of the selected template.

Figure 8:
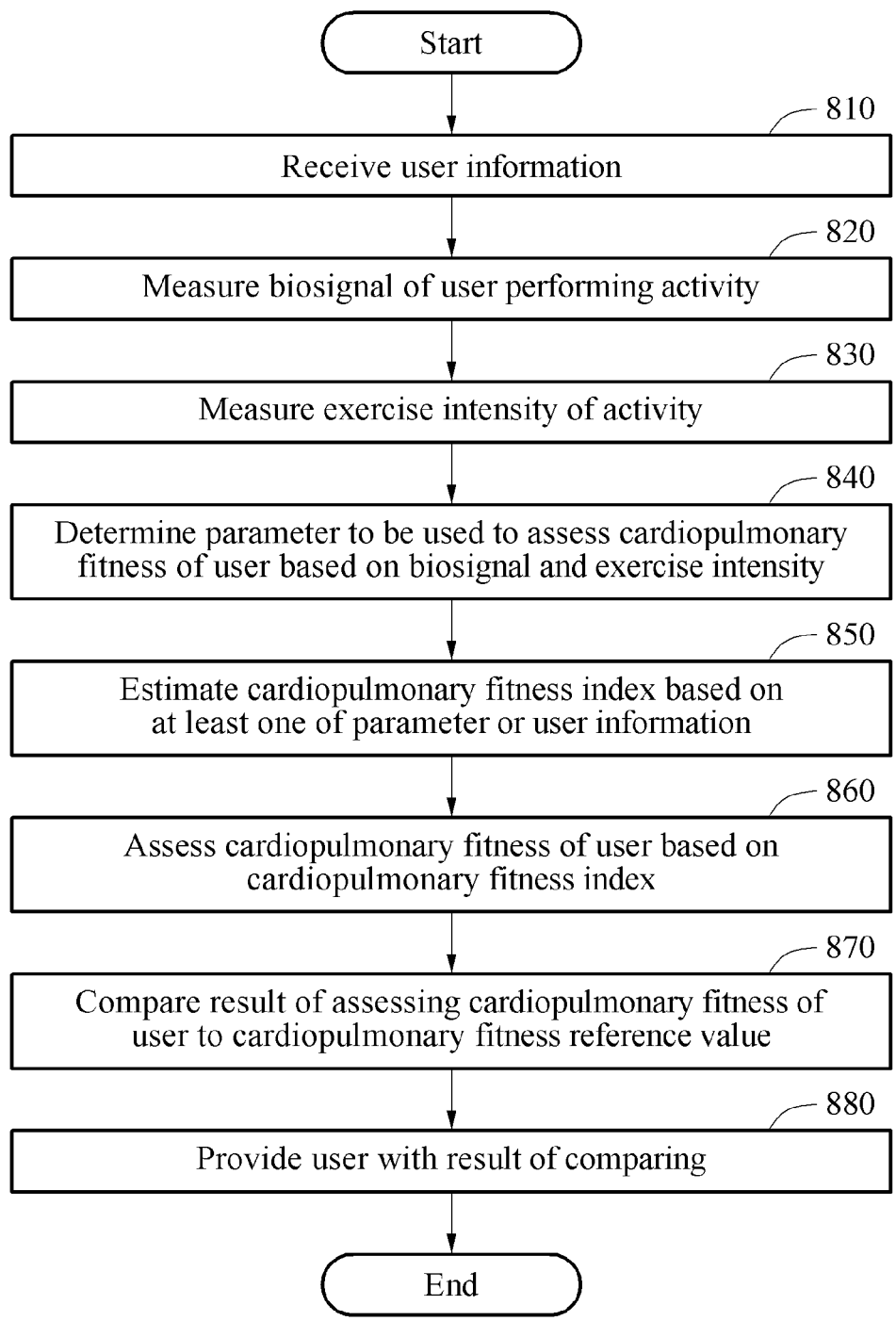

FIG. 8 is a flowchart illustrating an example of a method of assessing cardiopulmonary fitness.

Referring to FIG. 8, operations 810 through 860 are the same as operations 705 through 730 of FIG. 7, respectively. Thus, duplicated descriptions will be omitted for conciseness.

In operation 870, an assessing apparatus compares a result of assessing cardiopulmonary fitness of a user in operation 860 to a preset cardiopulmonary fitness reference value.

In operation 880, the assessing apparatus provides the user with a result of the comparing.

In an example, the assessing apparatus estimates a metabolic disease risk index, for example, a degree of risk, of the user based on a result of the assessing in operation 860, and provides the user with a health care prescription based on the metabolic disease risk index of the user. For example, the assessing apparatus determines whether the assessed cardiopulmonary fitness of the user or the cardiopulmonary fitness index is within a range of metabolic disease risk index pre-stored by gender or age. The assessing apparatus calculates a metabolic disease risk index or a health score of the user based on a result of the determining, and provides the user with a feedback. The assessing apparatus provides the user with a health care prescription such as an exercise prescription, a nutrition prescription, or a lifestyle prescription, for example.

In an example, a user may conveniently assess cardiopulmonary fitness by performing daily self-regulated activities, without setting aside a designated time to perform a specific exercise program designed for assessing the cardiopulmonary fitness of the user.

The mobile device, wearable device, assessing apparatus, measurer, processor, communication interface, input device, memory and other apparatuses or components shown in FIGS. 1A and 1B that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, antenna and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 2 and 5-8 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A processor-implemented method of assessing cardiopulmonary fitness, the method comprising:
    determining, using one or more processors, whether a biosignal of a user performing a self-regulated activity reaches a preset threshold;
    in response to the biosignal reaching the preset threshold, measuring, using one or more sensors, the biosignal and measuring, using one or more other sensors, an exercise intensity of the activity from when the biosignal reaches the preset threshold;
    determining, using the one or more processors, a relative biosignal by adjusting a level of the measured biosignal based on the measured exercise intensity;
    estimating, using the one or more processors, a cardiopulmonary fitness index based on the determined relative biosignal;
    assessing, using the one or more processors, the cardiopulmonary fitness of the user based on the cardiopulmonary fitness index;
    generating, using the one or more processors, either one or both of a personalized exercise program and a healthcare recommendation for the user based on a result of the cardiopulmonary fitness assessment; and
    outputting, to a communication interface, the either one or both of the exercise program and the healthcare recommendation for the user.

2. The method of claim 1, further comprising receiving an exercise perception level of the user,
    wherein the measuring of the biosignal comprises measuring the biosignal in response to a determination that the exercise perception level reaches a preset standard.

3. The method of claim 2, wherein the measuring of the exercise intensity comprises measuring the exercise intensity in response to a determination that the exercise perception level reaches the preset standard.

4. The method of claim 1, wherein the biosignal of the user comprises either one or both of a heart rate and a respiration rate.

5. The method of claim 1, wherein the exercise intensity comprises any one or any combination of any two or more of an exercise speed, an exercise distance, and revolutions per minute (RPM).

6. The method of claim 1, wherein the determining of the relative biosignal comprises calculating the relative biosignal based on a value obtained by dividing the biosignal by the exercise intensity.

7. The method of claim 1, further comprising:
receiving user information,
wherein the estimating comprises estimating the cardiopulmonary fitness index based on either one or both of the relative biosignal and the user information.

8. The method of claim 7, wherein the user information comprises any one or any combination of any two or more of a gender, an age, a height, a weight, a waist measurement, a waist-hip ratio, a body mass index, and a physical activity level of the user.

9. The method of claim 1, wherein the cardiopulmonary fitness index of the user comprises any one or any combination of any two or more of maximal oxygen consumption, a maximal heart rate, a ventilation threshold, and a lactate threshold.

10. The method of claim 1, further comprising:
comparing the assessed cardiopulmonary fitness to a preset cardiopulmonary fitness reference value; and
providing the user with a result of the comparing.

11. The method of claim 1, further comprising:
estimating a metabolic disease risk index of the user based on the assessed cardiopulmonary fitness of the user; and
providing the user with a health care prescription based on the metabolic disease risk index of the user.

12. The method of claim 1, wherein the outputting comprises providing the user with the personalized exercise program.

13. The method of claim 12, further comprising receiving preference information of the user, wherein the generating of the personal exercise program further comprises:
selecting a template from the preset exercise program templates based on the preference information;
adjusting an exercise intensity and an exercise duration of the selected template based on the assessed cardiopulmonary fitness of the user; and
generating the personalized exercise program based on the adjusted exercise intensity and the adjusted exercise duration of the selected template.

14. The method of claim 1, wherein the generating of the either one or both of the personalized exercise program and the healthcare recommendation further includes:
adjusting an exercise intensity and an exercise duration of a selected template based on the assessed cardiopulmonary fitness of the user, the selected template being selected, based on preference information of the user, from among the preset exercise program templates; and
generating the personalized exercise program based on the adjusted exercise intensity and the adjusted exercise duration of the selected template.

15. A processor-implemented method of assessing cardiopulmonary fitness, the method comprising:
determining, using one or more processors, whether a biosignal of a user performing a self-regulated activity reaches a preset threshold;
in response to the biosignal reaching the preset threshold, measuring, using one or more sensors, the biosignal and measuring, using one or more other sensors, an exercise intensity of the activity from when the biosignal reaches the preset threshold;
determining, using the one or more processors, a relative biosignal by adjusting a level of the measured biosignal based on the measured exercise intensity;
estimating, using the one or more processors, a cardiopulmonary fitness index based on the determined relative biosignal;
assessing, using the one or more processors, the cardiopulmonary fitness of the user based on the cardiopulmonary fitness index;
receiving, through a communication interface, preference information of the user;
selecting, using the one or more processors, a template from preset exercise program templates based on the preference information;
adjusting, using the one or more processors, an exercise intensity and an exercise duration of the selected template based on the assessed cardiopulmonary fitness of the user; and
generating, using the one or more processors, a personalized exercise program based on the adjusted exercise intensity and the adjusted exercise duration of the selected template; and
outputting, to the communication interface, the personalized exercise program.

16. A non-transitory computer-readable medium storing instructions that, when executed by a processor, cause the processor to perform a method of assessing cardiopulmonary fitness, the method comprising:
determining whether a biosignal of a user performing a self-regulated activity reaches a preset threshold;
in response to the biosignal reaching the preset threshold, measuring, using one or more sensors, the biosignal and measuring, using one or more other sensors, an exercise intensity of the activity from when the biosignal reaches the preset threshold;
determining a relative biosignal by adjusting a level of the measured biosignal based on the measured exercise intensity;
estimating a cardiopulmonary fitness index based on the determined relative biosignal;
assessing the cardiopulmonary fitness of the user based on the cardiopulmonary fitness index;
generating either one or both of a personalized exercise program and a healthcare recommendation for the user based on a result of the cardiopulmonary fitness assessment; and
outputting, to a communication interface, the either one or both of the exercise program and the healthcare recommendation for the user.

17. An apparatus for assessing cardiopulmonary fitness, the apparatus comprising:
one or more processors configured to:
determine whether a biosignal of a user performing a self-regulated activity reaches a preset threshold;
in response to the biosignal reaching the preset threshold, use one or more sensors to measure the biosignal and use one or more other sensors to measure an exercise intensity of the activity from when the biosignal reaches the preset threshold;
determine a relative biosignal by adjusting a level of the measured biosignal based on the measured exercise intensity;
assess the cardiopulmonary fitness of the user based on a cardiopulmonary fitness index estimated based on the parameter;

generate either one or both of a personalized exercise program and a healthcare recommendation for the user based on a result of the cardiopulmonary fitness assessment; and output, to a communication interface, the either one or both of the exercise program and the healthcare recommendation for the user.

18. The apparatus of claim 17, further comprising:

an input device configured to receive an exercise perception level of the user, wherein the one or more processors are configured to determine whether the exercise perception level reaches a preset standard, and the measurer is configured to measure the biosignal and the exercise intensity of the activity in response to a determination that the exercise perception level reaches the preset standard.

19. The apparatus of claim 17, further comprising:

a communication interface configured to receive user information, wherein the one or more processors are configured to determine the parameter based on a value obtained by dividing the biosignal by the exercise intensity and estimate the cardiopulmonary fitness index of the user based on either one or both of the parameter and the user information.

20. A processor-implemented method of assessing cardiopulmonary fitness, the method comprising:

determining whether a biosignal of a user performing a self-regulated activity reaches a preset threshold;

in response to the biosignal reaching the preset threshold, measuring the biosignal using one or more sensors from when the biosignal reaches the preset threshold;

determining a relative biosignal by adjusting a level of the measured biosignal based on an exercise intensity of the activity;

assessing the cardiopulmonary fitness of the user based on the determined relative biosignal;

generating either one or both of a personalized exercise program and a healthcare recommendation for the user based on a result of the cardiopulmonary fitness assessment; and outputting, to a communication interface, the either one or both of the exercise program and the healthcare recommendation for the user.

21. The method of claim 20, wherein the assessing of the cardiopulmonary fitness comprises obtaining a value corresponding to the biosignal divided by the exercise intensity.

22. The method of claim 20, wherein the assessing of the cardiopulmonary fitness comprises:

calculating a relative heart rate of the user based on the biosignal and the exercise intensity; and estimating a cardiopulmonary fitness index of the user based on user information.

23. The method of claim 20, wherein the determining of the exercise intensity comprises receiving information from one or more other sensors of a wearable device during the activity, and calculating the exercise intensity from the received information.

* * * * *